(12) United States Patent
Yu et al.

(10) Patent No.: US 9,867,632 B2
(45) Date of Patent: *Jan. 16, 2018

(54) MEDICAL INSTRUMENTS AND METHODS FOR FABRICATING SAME

(75) Inventors: Chris C. Yu, Conneautville, PA (US); Xuedong Du, Shanghai (CN)

(73) Assignee: Zhejiang Anpac Bio-Medical Science Co., Ltd., Lishui (CN)

(*) Notice: Subject to any disclaimer, the term of this patent is extended or adjusted under 35 U.S.C. 154(b) by 712 days.

This patent is subject to a terminal disclaimer.

(21) Appl. No.: 13/425,883

(22) Filed: Mar. 21, 2012

(65) Prior Publication Data

US 2012/0245568 A1 Sep. 27, 2012

Related U.S. Application Data

(60) Provisional application No. 61/466,076, filed on Mar. 22, 2011.

(51) Int. Cl.
| | |
|---|---|
| *A61B 17/32* | (2006.01) |
| *A61B 17/3209* | (2006.01) |
| *A61B 17/00* | (2006.01) |
| *A61M 13/00* | (2006.01) |
| *A61M 16/00* | (2006.01) |

(52) U.S. Cl.
CPC .......... *A61B 17/32* (2013.01); *A61B 17/3209* (2013.01); *A61B 2017/00526* (2013.01); *A61M 13/003* (2013.01); *A61M 16/00* (2013.01); *A61M 2205/0244* (2013.01); *A61M 2207/00* (2013.01); *A61M 2230/50* (2013.01); *Y10T 29/49826* (2015.01); *Y10T 29/49885* (2015.01)

(58) Field of Classification Search
CPC .................. A61M 5/2448; A61M 5/19; A61M 2005/1787; A61M 5/3294; A61M 25/04; A61M 2005/3267; A61M 5/2066; A61M 2025/0286; A61M 31/002; A61M 5/14276; A61M 11/06; A61M 37/0015; A61M 5/00; A61M 5/158

See application file for complete search history.

(56) References Cited

U.S. PATENT DOCUMENTS

| | | | |
|---|---|---|---|
| 5,317,938 A | 6/1994 | De Juan, Jr. et al. | |
| 6,503,231 B1 | 1/2003 | Prausnitz et al. | |
| 2002/0103412 A1* | 8/2002 | Trimmer | 600/16 |
| 2002/0116022 A1* | 8/2002 | Lebouitz | A61B 17/32 606/167 |
| 2002/0128570 A1* | 9/2002 | Bowman | A61B 5/01 600/567 |
| 2005/0049577 A1* | 3/2005 | Snell et al. | 604/544 |
| 2006/0105275 A1 | 5/2006 | Maloney et al. | |
| 2007/0178221 A1 | 8/2007 | Sims et al. | |

(Continued)

FOREIGN PATENT DOCUMENTS

TW 200840553 A 4/1996

OTHER PUBLICATIONS

The International Search Report and Written Opinion of the International Searching Authority for PCT/US2012/029931, (Corrected Version) date completed Sep. 18, 2012.

*Primary Examiner* — Duy Vu N Deo
(74) *Attorney, Agent, or Firm* — Weisun Rao; Greenberg Traurig, LLP

(57) ABSTRACT

The present invention provides novel medical instruments and methods for fabricating them by using nano-technology processes.

20 Claims, 26 Drawing Sheets

(56) References Cited

U.S. PATENT DOCUMENTS

2009/0176042 A1    7/2009  Cohen
2010/0087845 A1*  4/2010  Spiro ................ A61B 17/3211
                                                            606/167

* cited by examiner

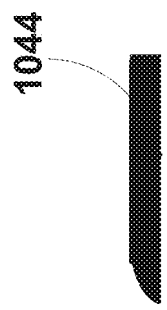
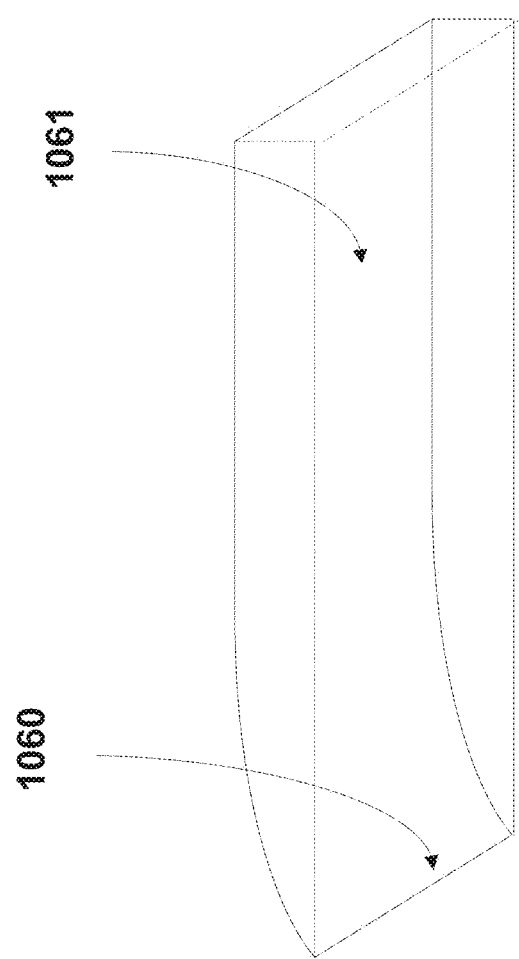
Figure 1(k)
Figure 1(l)

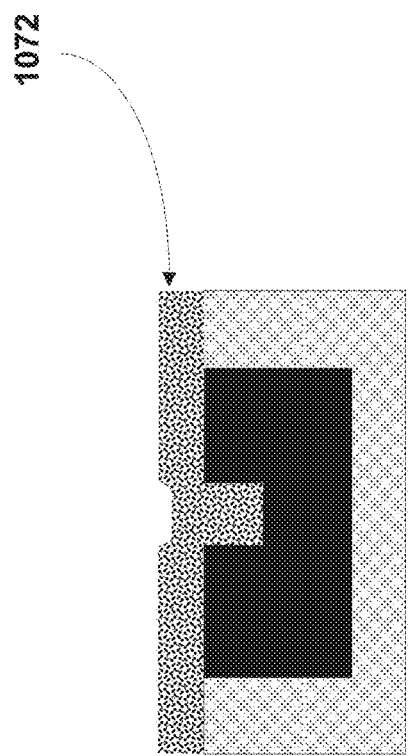
Figure 1(p)
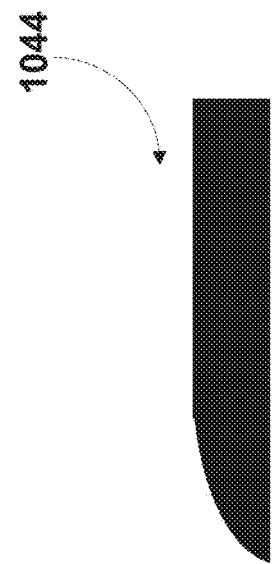
Figure 1(q)
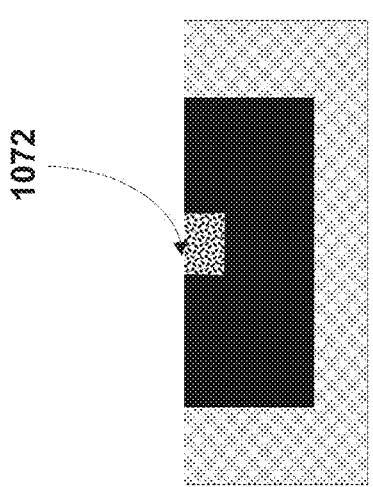

1091

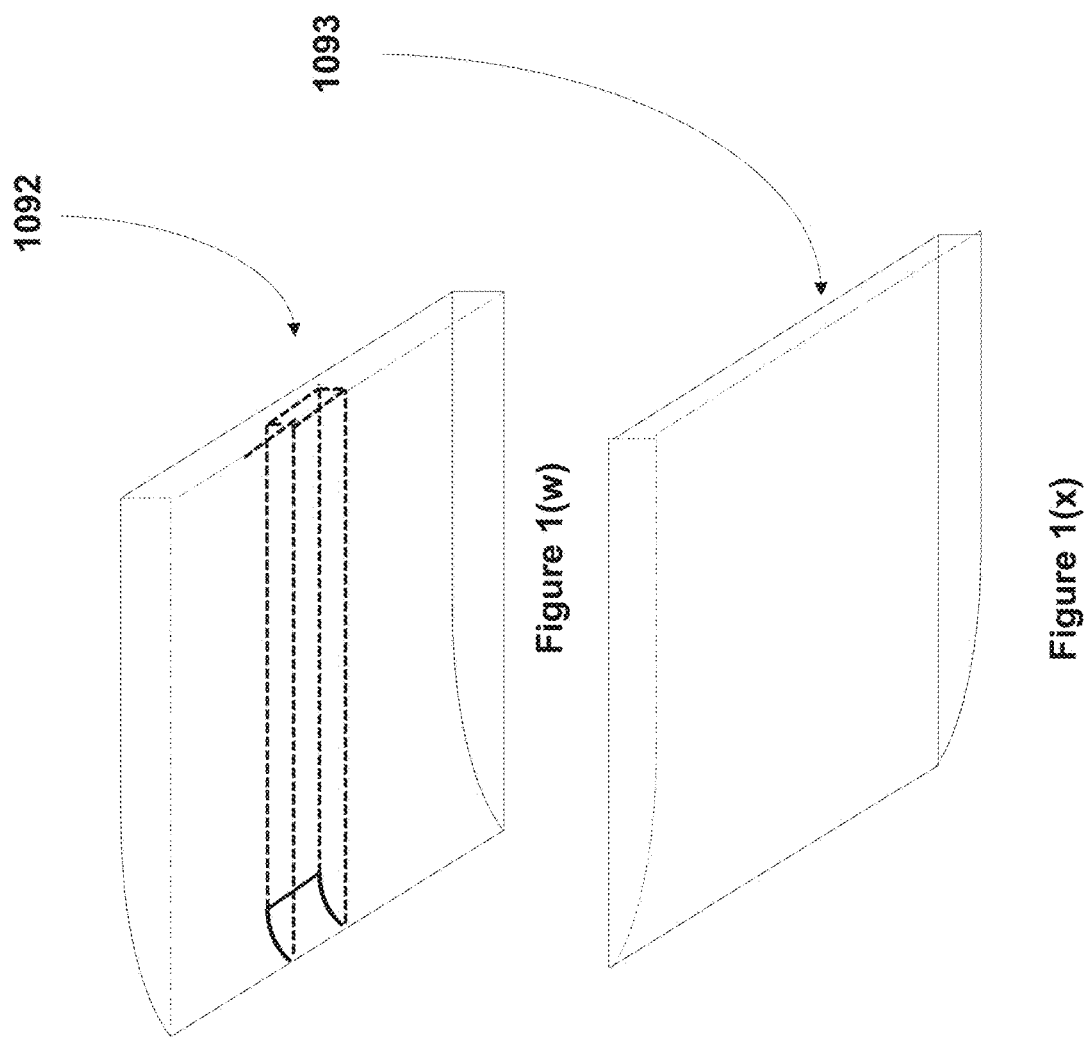

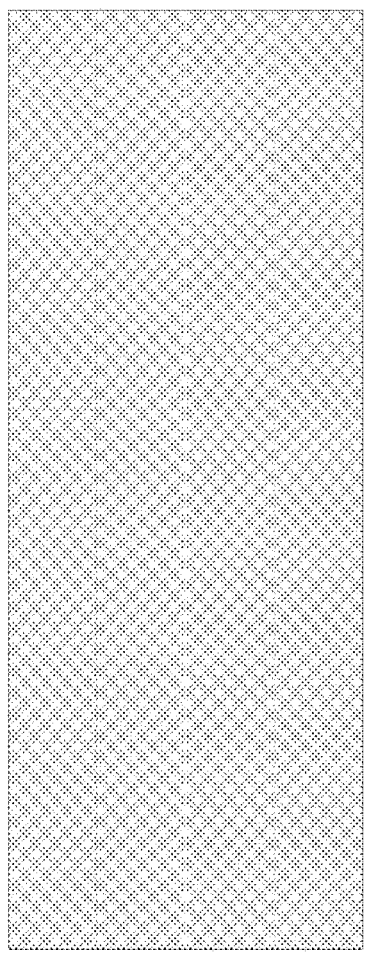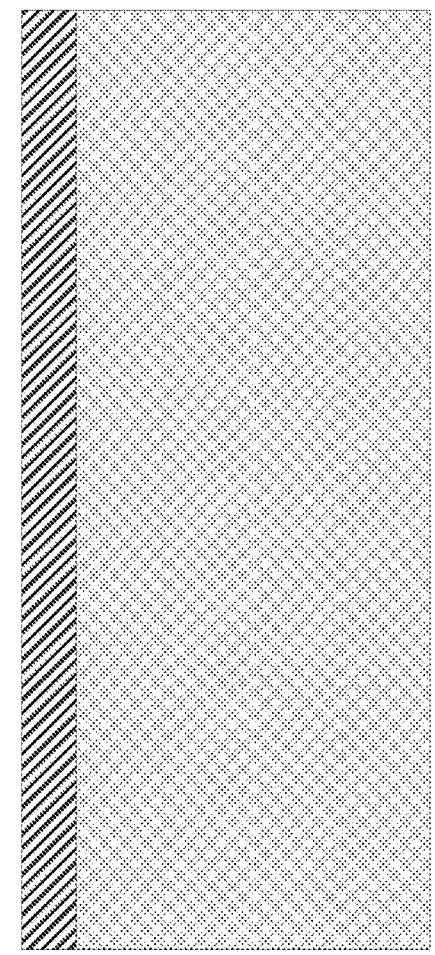

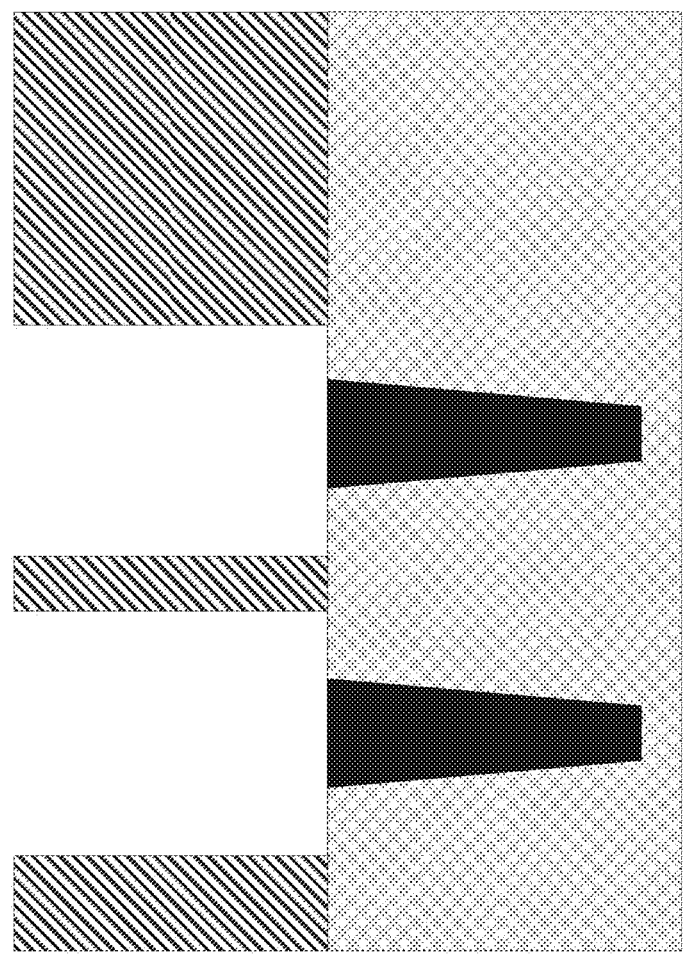

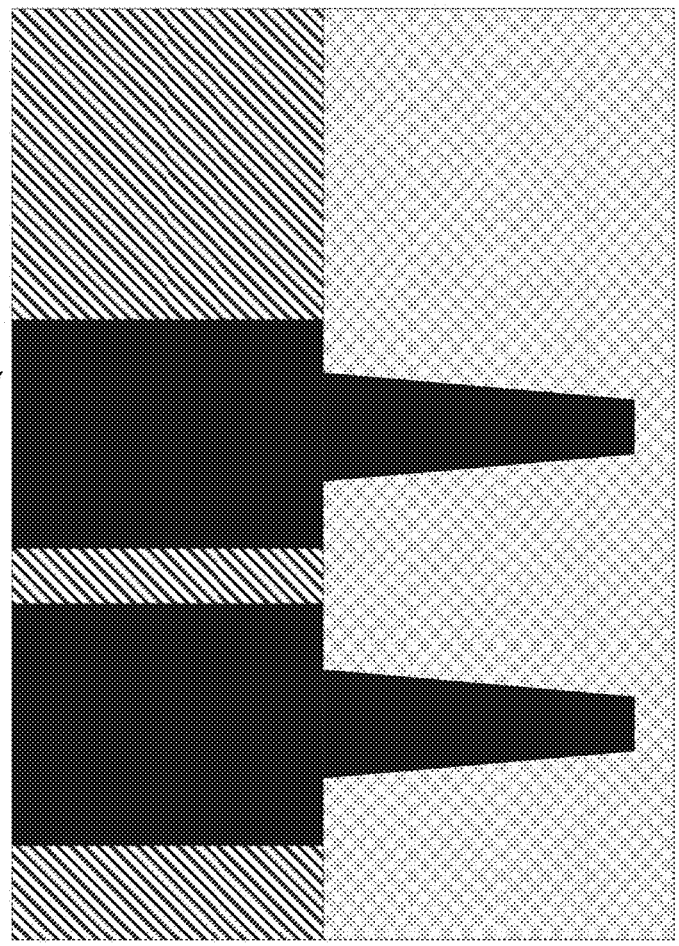

MEDICAL INSTRUMENTS AND METHODS FOR FABRICATING SAME

CROSS-REFERENCE TO RELATED APPLICATION

This application claims priority to U.S. Application No. 61/466,076, filed on Mar. 22, 2011, the contents of which are incorporated herein by reference in their entireties.

BACKGROUND OF THE INVENTION

In modern medicine, there are increasing needs for more advanced medical (including surgical) instruments with higher and more flexible functionalities. While there has been progress in micro-surgery in recent years, the current or traditional medical instruments have not been able to meet the most demanding requirements. For example, certain complex surgeries require a high degree of accuracy, while the current surgery instruments fails to meet this demand for not only lacking sufficient precision or functionalities, but also heavily relying upon manual operations.

Further, there are needs for lower cost medical instruments to reduce overall health cost. In some cases, medical instruments can only be disposable (one-time use) due to technical requirements and practical considerations, which requires a high volume, cost effective manufacturing technology.

Currently, most medical instruments for micro-surgeries are mechanical devices with single functionality, e.g., for cutting tissues or stitching a wound. These conventional surgical instruments, especially those with cutting edge, are mostly made in mass of metals such as stainless steel or tungsten. They are generally ground from harder materials such as diamonds, silicon and sapphire. See, e.g., US 2005/0188548 A1. Although this method is economic for making surgical blades, it has some challenges. For instance, the blade edge's sharpness lacks consistency and sometimes even varies significantly. A mechanical sharpening process will result in imperfections on the blade edge and thus is generally not able to lead to a superior sharp blade edge or a micro-miniature surgical blade. Further, one cannot use the process to carve second-order cutting edge structures such as desired asperities, serrations and inside angles.

A relatively new method for manufacturing surgical blade employs more advanced techniques in processing the stainless steel than grinding, in which the blade is then electrochemically polished to achieve a sharp edge. This process has been found to produce blades with a more consistent sharpness in the blade edge. However, the chemical process will still lead to imperfections on the surface of the blade by the corrosion, and the sharpness consistency is still to be improved for high-precision surgeries. As a result of these minute imperfections, a conventional steel surgical blade cannot cut tissues without tearing some of them. Such tearing of tissues during a surgery may slow down healing of the wound and even result in formation of scar tissue during and after the healing process.

Recently, a microelectronic fabrication methodology has been proposed for a micro-miniature tip assembly. It is fabricated using photolithography and anisotropic etching. Specifically, the crystalline form of silicon is used as advantage by etching along the grain boundaries to form a pit in a silicon substrate. Tungsten is then deposited into the pit to form a sharp tip for use in a scanning tunneling microscope assembly. However, the angle of the tip edge is determined and limited by the crystalline orientation angle of the silicon itself. Even if the substrate is switched to sapphire or ruby, the angle is still a constant which is determined by the crystal orientation of the substrate material. See, e.g., U.S. Pat. No. 4,916,002.

There have been a few other proposals for the manufacturing of surgical blades using silicon. See, e.g., US 2005/0266680 A1, U.S. Pat. No. 5,619,889, U.S. Pat. No. 5,579,583, and U.S. Pat. No. 7,728,089. However, in one form or another, these relatively newer processes are limited due to their inability to manufacture blades in various configurations and at a disposable cost. Many of these proposals are based on anisotropic etching of silicon which is highly directional, with different etch rates in different directions. Although this process can produce a sharp cutting edge, due to its very nature, it is still limited in not being able to attain certain blade shapes and bevel angles. Wet bulk anisotropic etching processes, such as those employing potassium hydroxide or hydroxyl potassium (KOH), ethylene-diamine/pyrcatechol (EDP) and trimethyl-2-hydroxethylammonium hydroxide (TMAH) baths, etch along a particular crystalline plane to achieve a sharp edge. This plane, typically in silicon, is angled 54.7° from the surface plane in the silicon wafers. This creates a blade with an included bevel angle of 54.7°, which has been found to be clinically unacceptable in most surgical applications as being too obtuse. This application is even worse when this technique is applied to making double bevel blades, as the included bevel angle is 109.4°. The process is further limited to the blade profiles that it can produce. The etch planes are arranged 90° to each other in the wafer. Therefore, only blades with rectangular profiles can be produced.

Further, most of the prior proposed surgical instruments are mechanical devices and are used as knives, tweezers, saws, pins, clamps, and hooks. They are not suitable for integrating with other devices having, e.g., physical, optical, electrical, chemical, thermal or acoustic functions.

The present invention aims to provide solutions to the above-described problems and challenges.

SUMMARY OF THE INVENTION

The present invention generally provides novel methods for fabricating medical or surgical instruments by using nano technologies (including, e.g., advanced semiconductor processing technologies, microelectronics technologies, microelectronic fabrication technologies) and medical or surgical instruments thus fabricated. Such medical instruments generally are of low costs and have high performance, higher degree of integration, high functionality, high degree of flexibility, high precision, high speed and automated.

In one aspect, these methods for fabricating medical instruments include use of one or more advanced semiconductor processing technologies such as, e.g., thin film deposition, lithography, etching (e.g., wet etching, dry etching, etc.), wet cleaning, ion implantation, diffusion, chemical mechanical polishing, packaging, or any combination thereof.

In another aspect, the methods for fabricating a medical instrument include the steps of: providing a substrate and optionally patterning the substrate to a desired profile; depositing a first material onto the substrate; optionally patterning the first material or the first material as well as the substrate to give the first material a first desired profile; and optionally etching and lifting off the patterned first material to give the medical instrument with the first desired profile.

In some embodiments, the substrate includes silicon, glass, germanium, sapphire, ruby, diamond, ceramic, or metal.

In some embodiments, the first material includes polysilicon, silicon dioxide, tungsten, titanium, aluminum, molybdenum, tantalum, or metal alloy, or any of their combinations as appropriate.

In some other embodiments, any of the profiles mentioned above can take the form of a blade, a handle, a drill, a column, a cone, a screw, a screw driver, a sheet, a knife, a saw, tweezers, a clamp, a hook, a hammer, a scraper, a suture, or a needle.

In some other embodiments, the method can further include the step of patterning the first material, before or after it is optionally patterned to the first desired profile, to give a second desired profile. For instance, the second desired profile thus patterned may comprise a trench in the second material.

In some other embodiments, the method can further include depositing multiple layers of thin film and patterning some of them, optionally removing (utilizing methods including but not limited to dry etching, wet etching, direct writing, molecular assembly, optical ablation, or polishing) at least one of the layers or a portion of one of the layers, to form desired profiles.

In still some other embodiments, the method may further include the step of coupling a medical instrument with the first desired profile with a medical instrument with or without the second desired profile.

In yet still some other embodiments, the method of this invention may further comprise the steps of: depositing a second material onto the first material, after the first material is first patterned, and patterning the second material to form the second desired profile.

In some embodiments, the method may further include the steps of: removing a portion of the patterned first material to leave the first material only in the recessed area of the patterned substrate; depositing a second material onto surface of the substrate (with recess area filled with the first material); patterning the second material and optionally the first material and the substrate, to give the second material a desired profile, and depositing a third material onto the second material, wherein the substrate is patterned to a desired profile before the first material is deposited onto the substrate, and the first, second, and third materials can be independently the same as or different from each other.

Still further, the method of this invention may include the step of: etching and lifting off the patterned first, second, and third materials together as the medical instrument.

Yet still further, the method of this invention may include the steps of: removing the third material to leave only a portion of the third material in the recessed area of the patterned second material; depositing a fourth material onto the second and third materials; patterning the fourth material and optionally the first and second and third materials and the substrate, to give the fourth material a desired profile; and depositing a fifth material onto the fourth material, wherein the first, second, third, fourth, and fifth materials can be independently the same as or different from each other.

Still additionally, the method may include the step of etching and lifting off the patterned first, second, third, fourth, and fifth materials together as the medical instrument.

In some embodiments, any of the deposited materials can independently comprise polysilicon, piezo-electric materials, optical materials, thermal materials, electro-optical materials, silicon dioxide, doped silicon dioxide, silicon nitride, silicon carbide, glass, diamond, tungsten, titanium, aluminum, molybdenum, tantalum, metal alloy, or any combination thereof where possible or applicable.

In some other embodiments, the step of patterning comprises lithography, etching, chemical polishing, mechanical polishing, chemical mechanical polishing, direct writing, molecular assembly, optical ablation, dry etching or wet cleaning. The wet etching process can be conducted, e.g., with a solution comprising hydrofluoric acid, sulfuric acid, phosphoric acid, buffered oxide etch solution (BOE), ammonium fluoride, hydrogen peroxide, hydroxyl potassium, ammonia, or nitric acid.

In still some other embodiments, the method of this invention may further include the steps of: integrating the medical instrument to a device selected from the group consisting of sensors for detecting electric, magnetic, electromagnetic, thermal, optical, acoustical, biological, chemical physical, or mechanical properties; microelectronic modules; surgical instruments, gyro meters or gyro compasses; memory chips; logic processing chips; application specific chips; communications components; and micro-drug-containers.

In another aspect, the present invention provides medical instruments fabricated by a method of this invention.

In some embodiments, the size of these medical instruments may range from about 1 angstrom to about 10 centimeters, e.g., from 5 angstroms to 0.5 centimeter, from 100 angstroms to 10 micrometers, from about 1 micron to about 2 centimeters.

In some other embodiments, the medical instrument may be a surgery knife, a surgical drill, a surgical saw, surgical tweezers, a surgical clamp, a surgical hook, a surgical hammer, a scraper, a needle, a blade, a tongue depressor, a medical thermometer, a blood sugar meter, an artificial heart, a fibrin scaffold, a stent, a treadmill, an ultrasound sensor, a phototherapy unit, an endoscope, a human-implantable RFID chip, a laparoscopic insufflator, a phonocardiograph, a radiant warmer, an electronic thermometer, a breast pump, a surgical microscope, an ultrasonic nebulizer, a temperature monitor, a ventilator, an auto transfusion unit, a cardiac defibrillator, an (external or internal) electrosurgical unit, an external pacemaker, a fetal monitor, suture, or an integrated medical instrument thereof.

In some other embodiments, the medical instrument can be integrated with a micro blade, a probing channel, a data wiring, or a central controlling circuitry unit. Alternatively or additionally, the instrument can be further packaged to provide support for the structural construction of the integrated medical instrument or to for integrate the device components together.

In some embodiments, sensors can be installed in the probing channel to detect or measure an electrical, magnetic, electromagnetic, thermal, optical, acoustical, biological, chemical, electro-mechanical, electro-chemical, electro-optical, electro-thermal, electro-chemical-mechanical, biochemical, bio-mechanical, bio-optical, bio-thermal, biophysical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical, or mechanical property, or a combination thereof, of a biological subject. For example, the electrical property can be surface charge, surface potential, resting potential, electrical current, electrical field distribution, electrical dipole, electrical quadruple, three-dimensional electrical or charge cloud distribution, electrical properties at telomere of DNA and chromosome, capacitance, or impedance; the thermal property can be temperature or vibrational frequency; the optical property can be optical absorption, optical transmission, optical reflection, optical-electrical property, brightness, or fluorescent emission; the chemical property can be pH value, chemical reaction, bio-chemical reaction, bio-electro-chemical reaction, reaction speed, reaction energy, speed of reaction, oxygen concentration, oxygen consumption rate, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property can be density, shape, volume, or surface area; the biological property can be surface shape, surface area, surface charge, surface biological property, surface chemical property, pH, electrolyte, ionic strength, resistivity, cell concentration, or biological, electrical, physical or chemical property of solution; the acoustic property can be frequency, speed of acoustic waves, acoustic frequency and intensity spectrum distribution, acoustic intensity, acoustical absorption, or acoustical resonance; the mechanical property can be internal pressure, hardness, flow rate, viscosity, shear strength, elongation strength, fracture stress, adhesion, mechanical resonance frequency, elasticity, plasticity, or compressibility.

In some other embodiments, the central controlling circuitry unit can include microelectronic modules such as, e.g., a signal amplifier, a processing unit, a signal lock-in unit, a signal processing unit, a communication unit, a logic processing unit, and a memory device (e.g., a chip), to collect information and transmit it to a server. In some other embodiments, the communication unit can include microelectronic modules such as, e.g., a signal receiver, a signal transmitter, a signal encoding, and a signal decoding unit.

In yet still some other embodiments, a gyro meter or a gyro compass can be installed in the central controlling circuitry unit, to precisely trace the location of the blade. Multiple channels can be integrated in a blade and can be packaged together, to detect multiple properties of a tissue in contact with the medical instrument.

In some other embodiments, a channel is in one end integrated with the blade and in the other end connected with a micro-drug-container by a tunnel. The micro-drug-container can release a desired amount of the drug when the biological information of the sensor is analyzed by the central controller and the drug is in need.

The novel medical instruments fabricated using the methods disclosed in this application can be used for surgeries of external wound, and internal diseases, specifically for eye, skin, brain, cancer, heart, liver, stomach, intestine, and lung surgeries.

As used herein, the term "medical instrument" is interchangeable with the term "surgical instrument" and generally refers to an instrument with a medical application, e.g., for surgery or for diagnosis.

As used herein, the term "a biological subject" refers to, e.g., a single cell or a single biological molecule such as DNA or RNA, protein, a virus, an organ, or a tissue.

As used herein, the term "or" has the meaning of both "and" and "or."

As used herein, the meaning of a singular noun includes that of a plural noun and thus a singular term, unless otherwise specified, may also carry the meaning of its plural form.

As used herein, the term "deposit" or "depositing" is meant to apply a thin film material to a surface. A deposition can be chemical or physical. In chemical deposition, a fluid precursor undergoes a chemical change at a solid surface, leaving a solid layer. An everyday example is the formation of soot on a cool object when it is placed inside a flame. Since the fluid surrounds the solid object, deposition happens on every surface, with little regard to direction; thin films from chemical deposition techniques tend to be conformal, rather than directional. By contrast, physical deposition uses mechanical, electromechanical or thermodynamic means to produce a thin film of solid. An everyday example is the formation of frost. Since most engineering materials are held together by relatively high energies, and chemical reactions are not used to store these energies, commercial physical deposition systems tend to require a low-pressure vapor environment to function properly; most can be classified as physical vapor deposition. Examples of deposition methods in semiconductor processing include vacuum evaporation, sputtering, and chemical vapor deposition.

As used herein, the term "pattern" or "patterning" refers to the process (chemical or physical) for treating a material to give rise to a certain physical parameter, e.g., shape, configuration, weight, depth, etc. The physical process can be, e.g., mechanical polishing or graving; and the chemical process can be, e.g., etching (dry or wet), lithography, chemical polishing, molecular self assembly. Other processes can be laser ablation, direct writing, electron beam writing, X-ray writing, and chemical mechanical polishing.

As used herein, the term "etch" or "etching" refers to a process of using a strong acid, a mordant, or another chemical, to cut into or preferential chemical reaction with the unprotected parts of a material's surface to create a design in intaglio in the material (e.g., metal or silicon). Examples of etching processes include wet etching and dry etching (such as reactive ion etching).

As used herein, the term "chemical mechanical polishing" or "planarization" refers to a process of planarizing (polishing) a surface with the combination surface chemical reaction and mechanical abrasion.

As used herein, the term "package" or "packaging" refers to a molded casing inside which is embedded one or more discrete or integrated components which may be connected and used within an electronic circuit, or the integration of different devices into one single medical instrument.

Unless otherwise defined herein, all terms recited in this document should carry their general meanings as known to a skilled person in the art to which this invention pertains.

DETAILED DESCRIPTION OF THE INVENTION

Figure 1A:
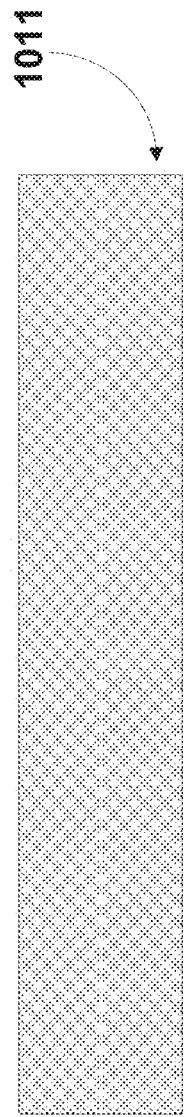
FIG. 1 illustrates an example of the method of this invention.
Figure 1B:
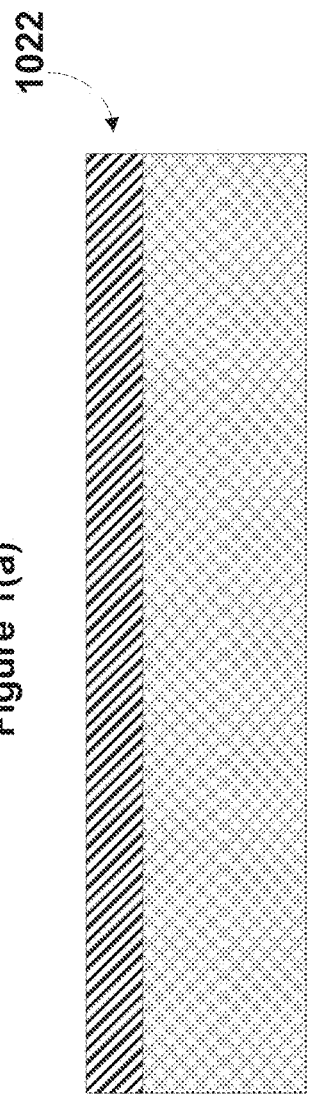
Figure 1C:
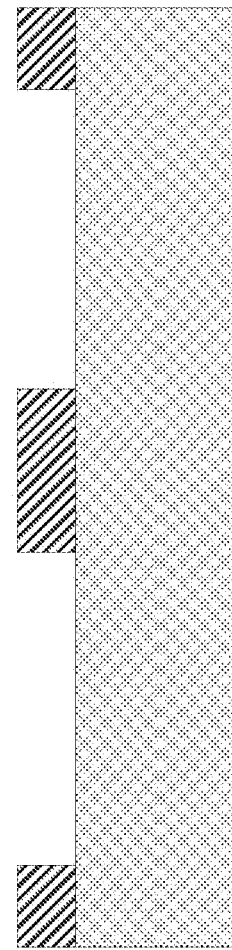
Figure 1D:
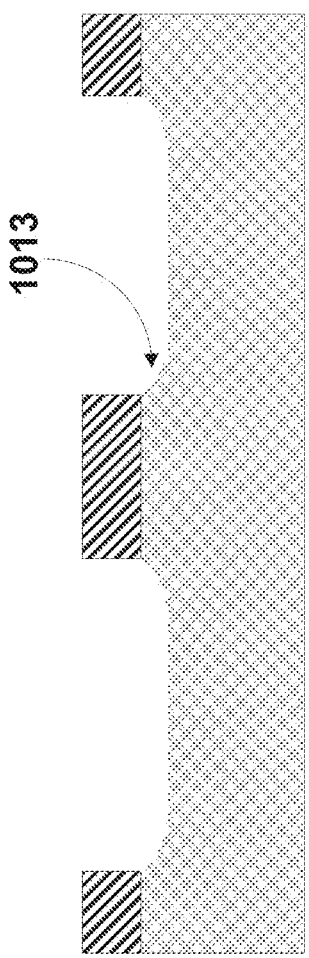
Figure 1E:
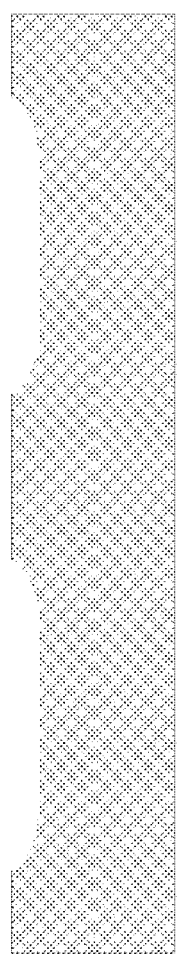
Figure 1F:
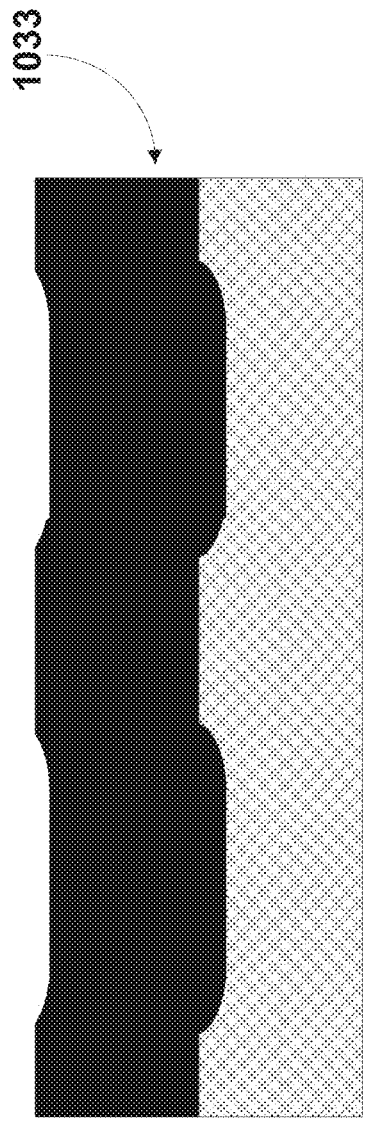
Figure 1G:
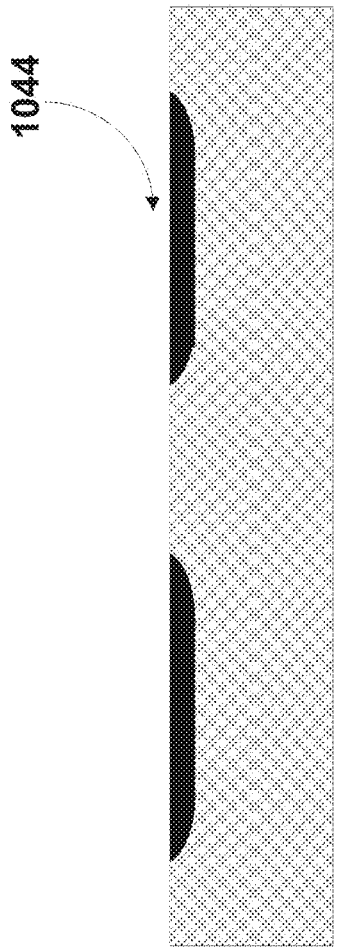
Figure 1H:
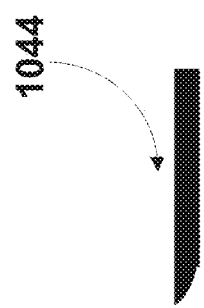
Figure 1I:
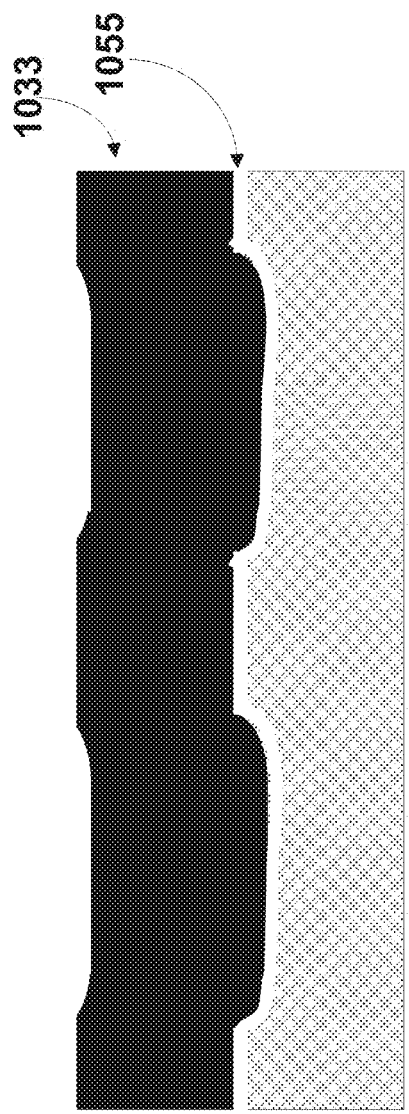
Figure 1J:
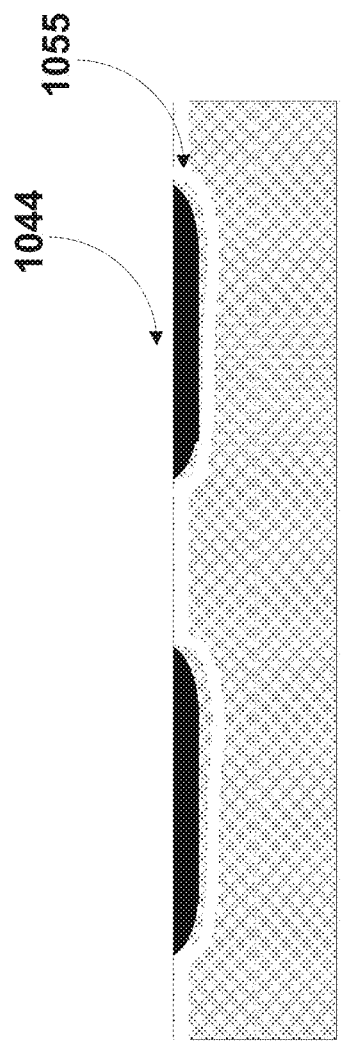
Figure 1M:
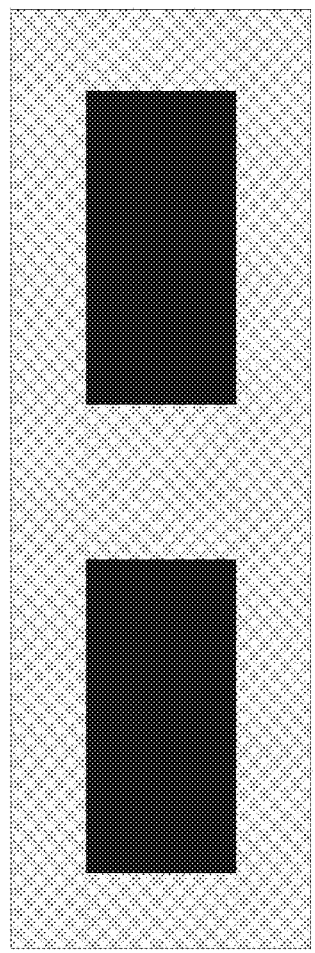

Compared to conventional methods, the novel methods provided by this invention allow for fabricating medical instruments with controlled features, uniquely improved properties, enhanced precision, desired profiles, different functionalities, and at a lower cost. For instance, the medical instruments thus obtained can feature a size as small as sub-micron which would significantly enhance the ability, effectiveness, and accuracy of medical or surgical operations such as a micro-surgery. Further, various types of medical instruments of different functions can be fabricated by a method of this invention and integrated onto a single medical device (for example, a sensor, a knife, a cleaner, and a suture can be integrated into the one instrument), thus creating a sophisticated and powerful medical device with advanced or multi-functions. This in turn enables a higher degree of automation in medical operations. As such, the present invention provides methods for making medical instruments with improved features such as, e.g., better performance, higher degree of integration, more functionalities, more flexibility, and high-volume production at lower costs.

In an embodiment, the method provided by this invention can be used for fabricating high-performance and low-cost surgical knives for operations on eyes. In an example of this method, a first material is deposited onto a substrate as a thin film; the first material is then patterned, e.g., by lithography and etching technologies. The patterned first material can then be lifted off, e.g., after a selective etch process (between the substrate and the first material). Optionally, before the first patterned material is lifted off, a second material can be deposited onto the first material, subsequently patterned (e.g., by a chemical mechanical polishing process); and then the patterned second material (optionally together with the patterned first material) can then be lifted off, e.g., after a selective etch process between the first material and the second material or between the substrate and the first material). Also optionally, a liner material can be deposited following the deposition or patterning of the first material, and an etch specific to the liner material can be used to lift off the first or second material or their combination. Alternatively, in this process, patterning of the second thin film material can be used in combination with the said chemical mechanical polishing process.

In another embodiment, the method of this invention can be used to fabricate a surgical knife integrated with a sensor, a cleaner, and a suture. For example, during the patterning of one of the materials, a specific profile (e.g., a trench) can be created and a sensor or a clearer can then be included in the trench, thus giving the integrated medical instrument. Optionally, the medical instrument can also include an injector with a drug vessel.

In yet another embodiment, the method of this invention can be used to fabricate a medical instrument that includes a sensor, an integrated circuit unit with memory and logic functions, at least one surgical unit (e.g., a knife, a blade, a laser, etc.), a cleaning unit, a suture, and a drug release unit. Optionally, the medical instrument can operate in an automated mode for micro-surgery.

Examples of medical instruments that can be fabricated by using the method of this invention include, but are not limit to, surgical knives, surgical drills, surgical saws, blade, tongue depressors, medical thermometers, blood sugar meters, artificial hearts, fibrin scaffolds, stents, treadmills, ultrasound sensors, phototherapy units, endoscopes, human-implantable radio-frequency identification (RFID) chips, laparoscopic insufflators, phonocardiographs, radiant warmers, electronic thermometer, breast pumps, surgical microscope, ultrasonic nebulizers, temperature monitor, ventilators, auto transfusion units, cardiac defibrillator, external or internal electrosurgical units, external pacemaker, fetal monitors, ventilator, and suture.

The novel medical instruments fabricated using the methods disclosed in this application can be used for surgeries of external wound, and internal diseases, specifically for eye, skin, brain, cancer, heart, liver, stomach, intestine, and lung surgeries.

FIGS. 1-5 further illustrate examples of the methods and medical instruments of this invention.

Specifically, FIG. 1 illustrates a specific example of the methods of this invention. In this example, a substrate 1011 is provided (FIG. 1(a)) and then coated with a first material 1022 which is light sensitive (e.g., a photoresist) as shown in FIG. 1(b). The first material 1022 is subsequently exposed and developed in a lithography process flow, to give itself a desired pattern (see FIG. 1(c)). The substrate 1011 is next etched (e.g., wet etching or dry etching) to a desired profile 1013. In generally, wet etching provides better control for the desired profile than dry etching. A second material 1033 is then deposited onto the patterned substrate 1011 (see FIG. 1(f), and then polished by a chemical mechanical polishing process to leave in the recessed substrate area 1044 (see FIG. 1(g)), which is a designed medical instrument. An etching process is then used to lift off the medical instrument 1044 (FIG. 1(h)). This etching process is preferably selective to the medical instrument 1044 (higher etching rate for substrate 1011) and either wet etching or vapor etching can be used (for a high etch rate of the substrate material 1011 to the second material 1033). Sometimes, to facilitate lift-off of the medical instrument, a liner material 1055 can be deposited following the patterning of the substrate 1011 and before the deposition of the second material 1033 (see FIG. 1(i)). Following the deposition and polishing of the second material 1033, an etching process can be used to selectively remove the liner material 1055 (see FIG. 1(j)), thereby lifting off the medical instrument 1044 (see FIG. 1(k)).

FIG. 1(k) is a front end cross-sectional view of the medical instrument 1044 (e.g., a surgery blade in this case) and FIG. 1(l) is a perspective view of the drawing of the medical instrument 1044. In FIG. 1(l), the section 1060 represents the blade bevel and the section 1061 represents the area of the blade for mounting to a cantilever or manipulator.

Enhancements of the medical instrument or surgical blade are illustrated in the rest of FIG. 1. FIG. 1(g) gives a front end cross-sectional view of the medical instrument 1044 while FIG. 1(m) gives a top plan view of the same medical instrument 1044.

Optionally, a hard mask can be first formed on the substrate 1011, and a reaction process can be carried out on the substrate surface next to form a compound layer through the said reaction with the substrate 1011. One example is the use of a silicon substrate in which the silicon substrate can react chemically (e.g., by an oxidation process) with a steam (e.g., containing oxygen) to form a silicon dioxide surface layer, forming a so-called bird beak feature which can be optimized via process tuning to result in a desired profile for medical applications.

Figure 1N:
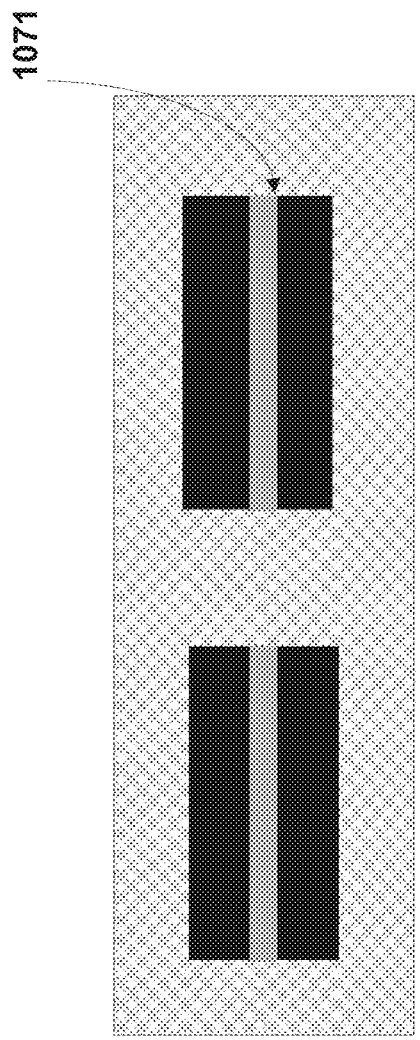
Figure 1O:
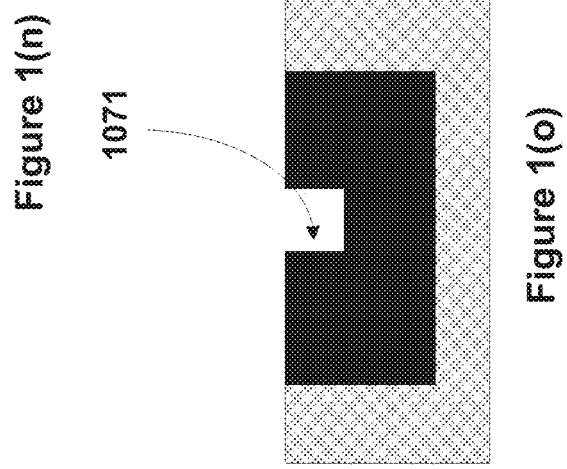

Through lithography and etch (wet or dry) processes, a trench 1071 can be formed on the medical device 1044. FIG. 1(n) is the top plan view of the medical device 1044 with the trench 1071 while FIG. 1(o) is its side cross-sectional view.

Figure 1R:
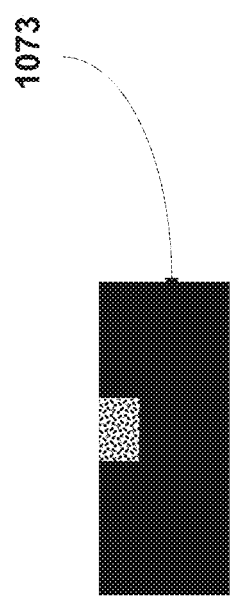
Figure 1S:
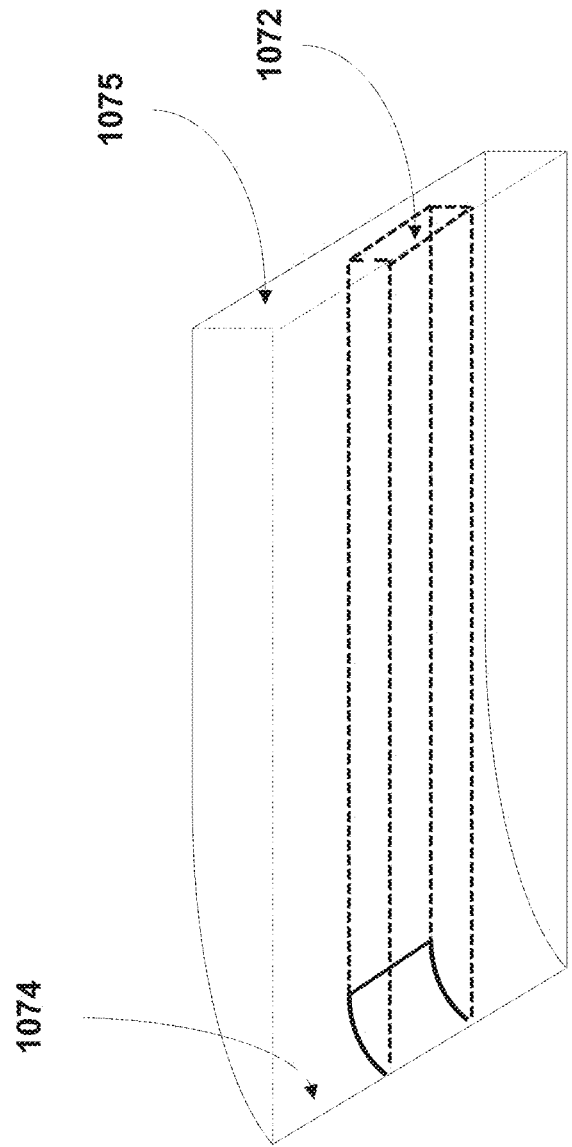
Figure 1T:
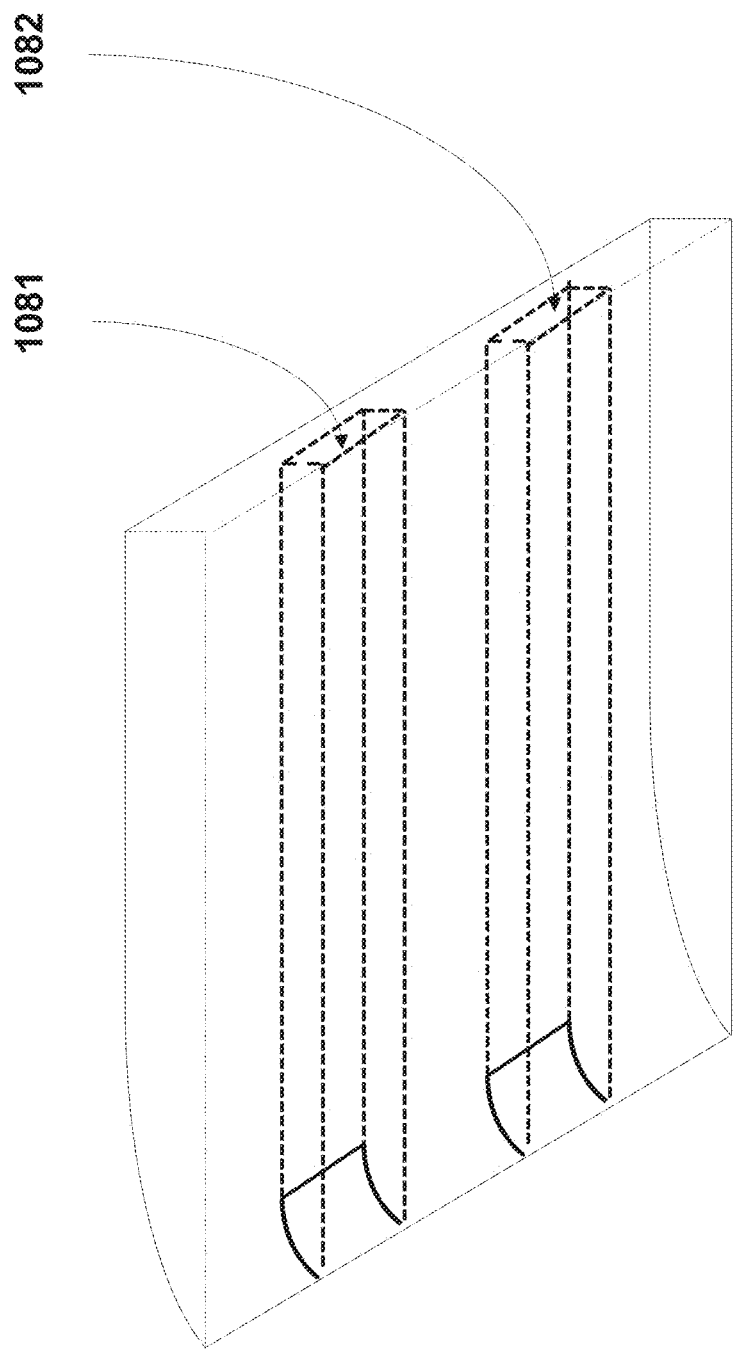

An additional material 1072 is then deposited onto the trenched blade (see FIG. 1(p)), and then a planarization process of this additional material 1072 is followed (see FIG. 1(q)) which gives rise to a new, enhanced instrument 1073. The new instrument has a trench 1071 filled with a material 1072 different from the foundation material for the initial medical instrument 1044. It can then be lifted off following the same etching process as previously described for 1044. FIG. 1(r) is a side cross-sectional view of the enhanced medical instrument 1073, while FIG. 1(s) provides a perspective view of the same enhanced medical instrument 1073. Shown in FIG. 1(s), the section 1074 is the bevel of the new, enhanced blade or medical instrument 1073, while the section 1075 is the area for mounting to a cantilever or manipulator.

The additional material 1072 can be wired with an analyzing circuitry, a signal generator circuitry, or both, for additional functions. When the additional material 1072 is an electrical conductive material, it can sense the electrical properties of a tissue. When the additional material 1072 is an optical transparent material, it can serve as an optical fiber and transmit the image information of the tissue. If the additional material 1072 is a piezoelectric material, it can sense and transmit acoustic signals of the tissue. This sensing and transmitting principle can be extended to carry multiple probing channels in the cutting edge of the blade (e.g., 1081 and 1082 in FIG. 1(t)) and the blade can then pulse multiple signals to the tissue and sense the feed back signals.

Figure 1U:
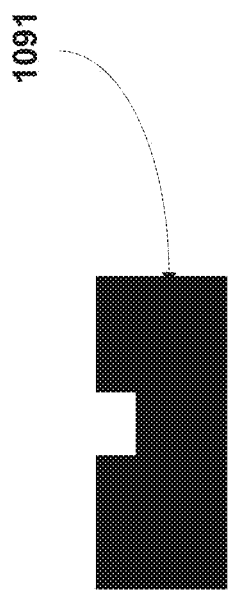
Figure 1V:
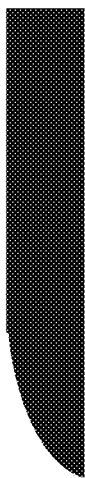
Figure 1Y:
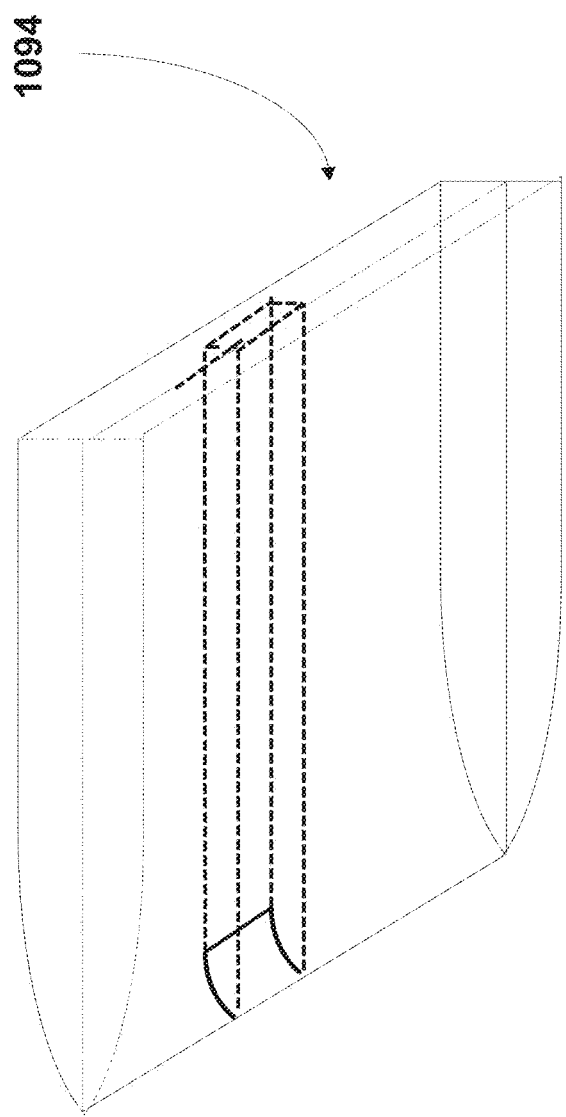
Figures 2C, 2D:
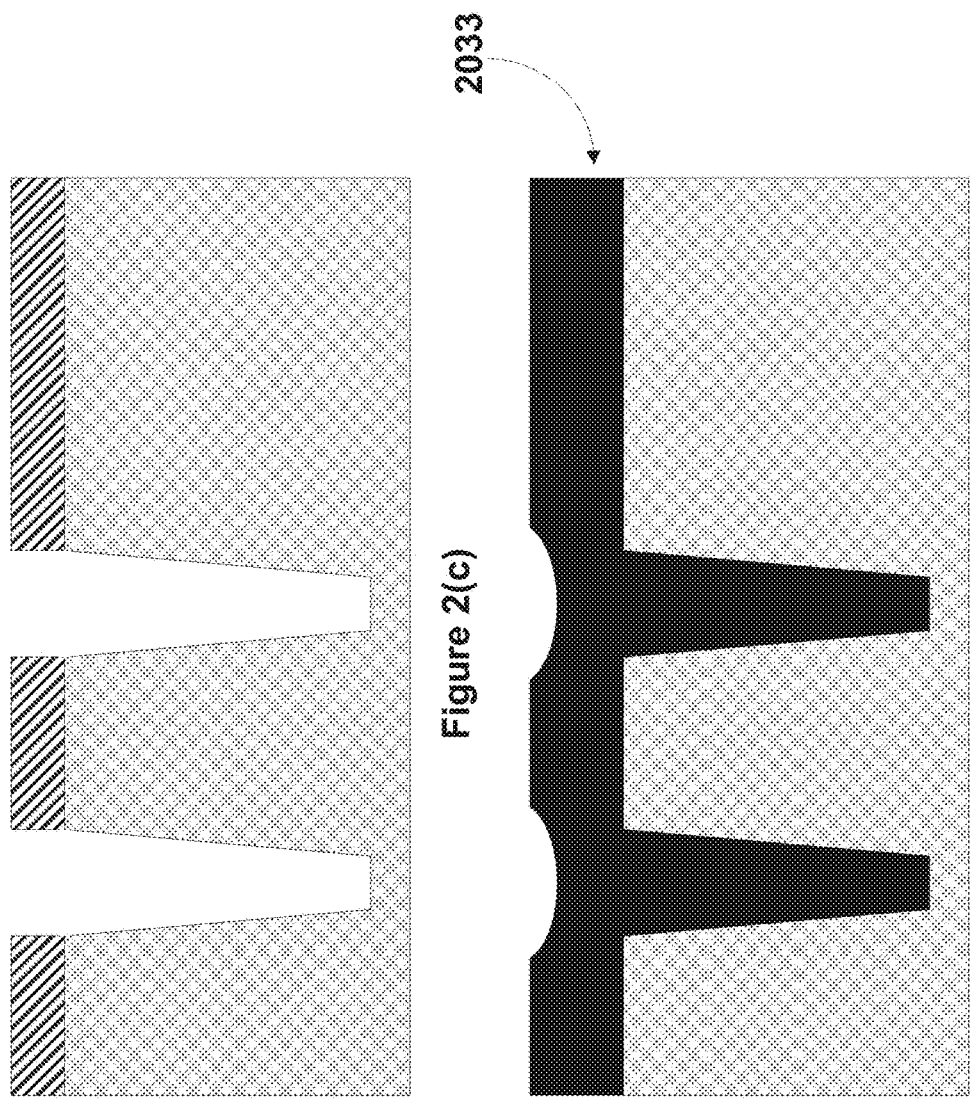
FIG. 2 illustrates another example of the method of this invention.
Figure 2E:
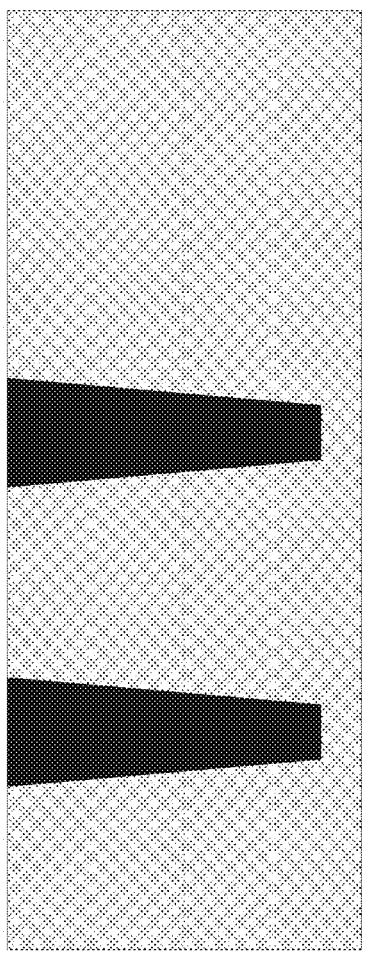
Figure 2F:
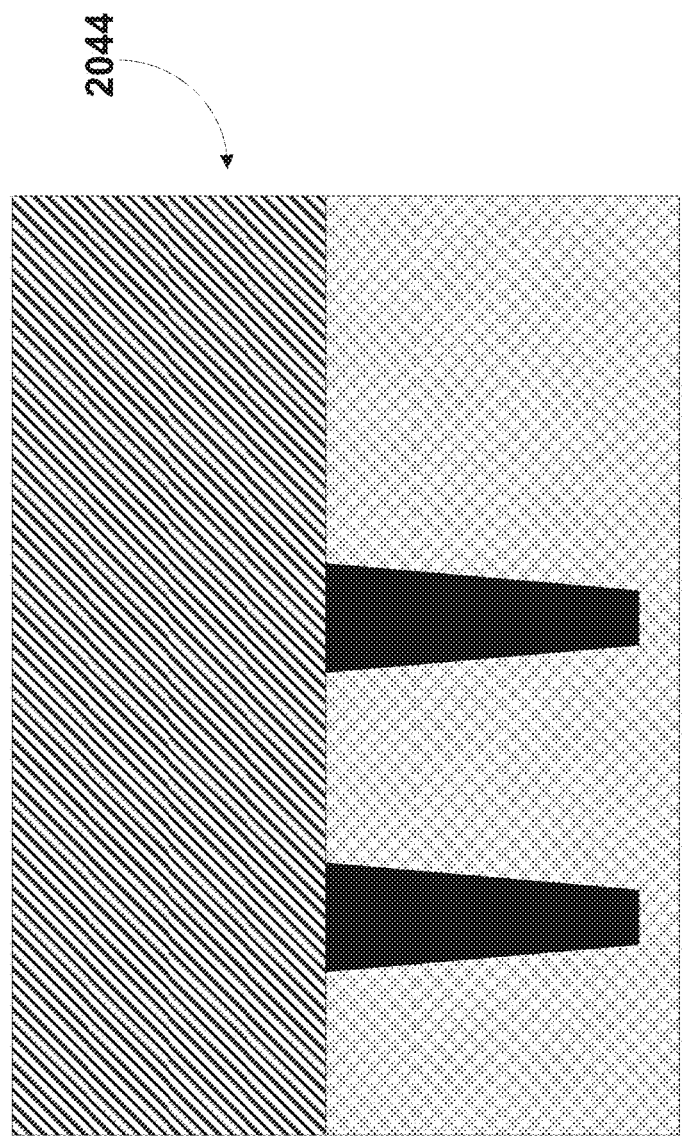
Figure 2H:
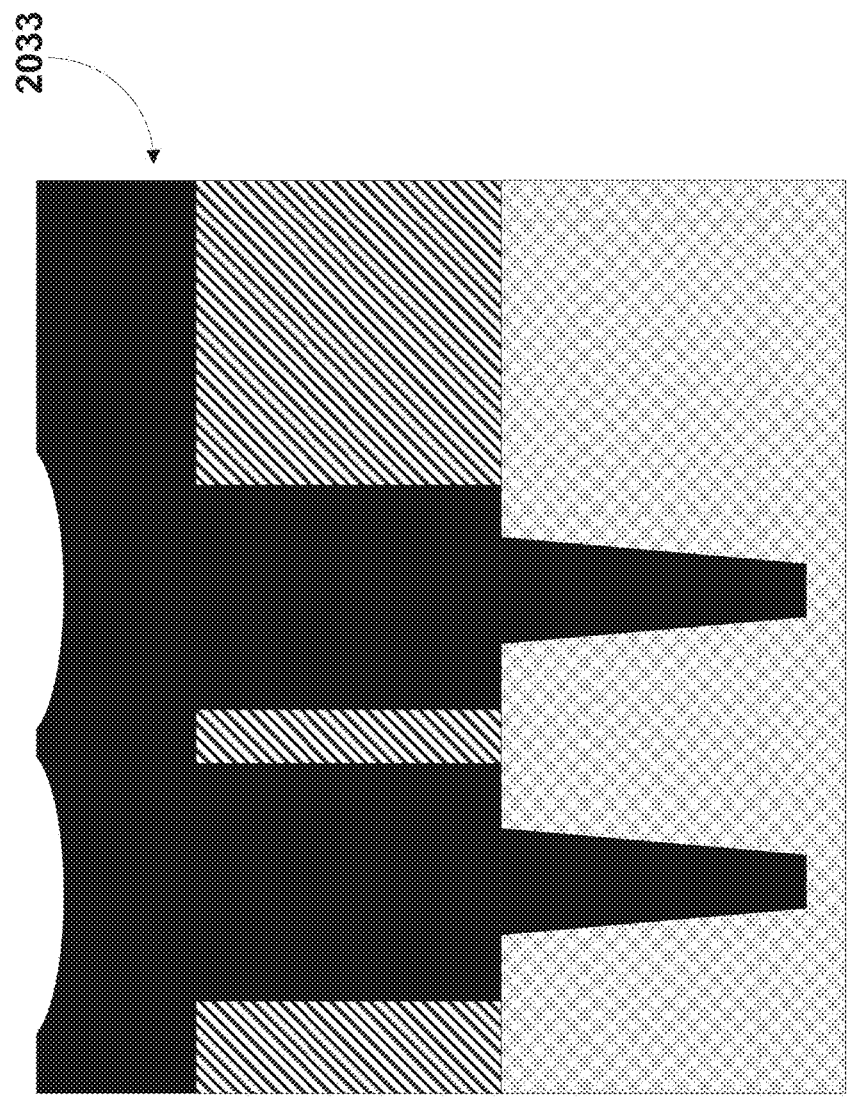
Figure 2J:
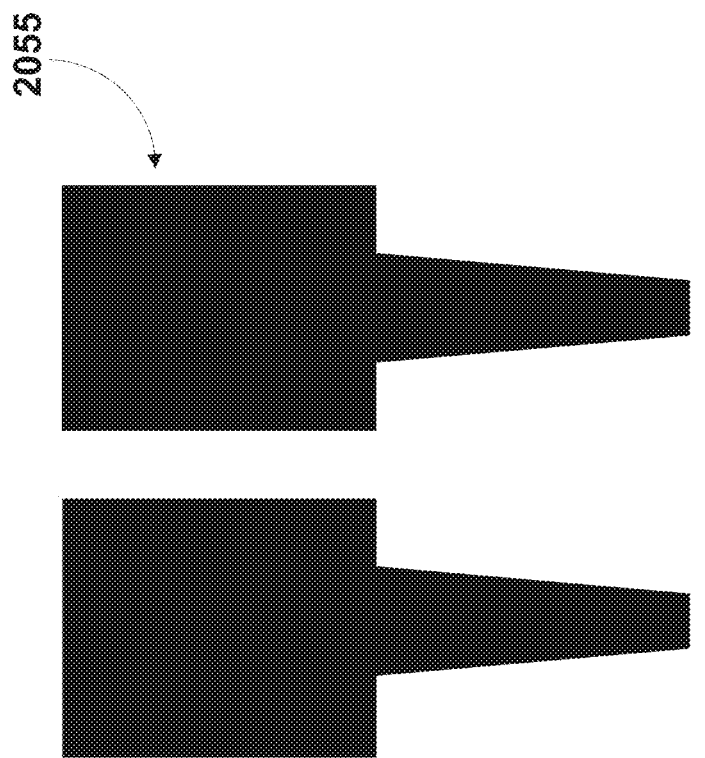
Figure 3A:
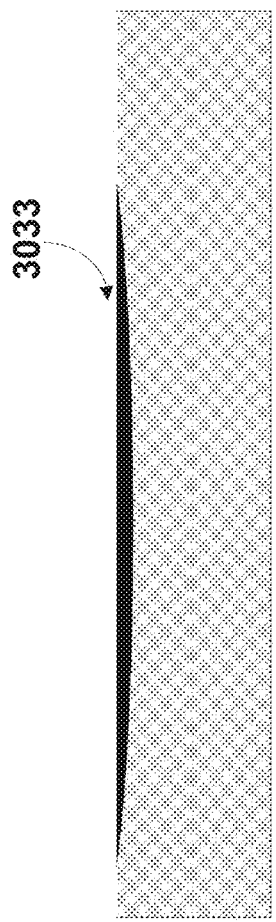
FIG. 3 illustrates another example of the method of this invention which gives rise to medical instruments of various profiles.
Figure 3B:
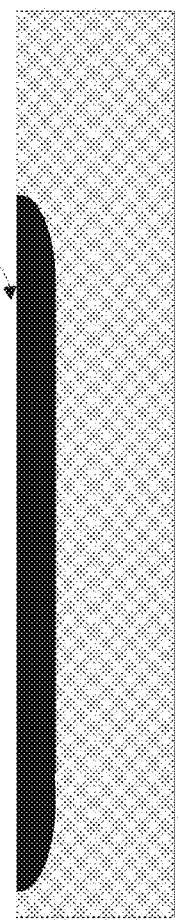
Figure 3C:
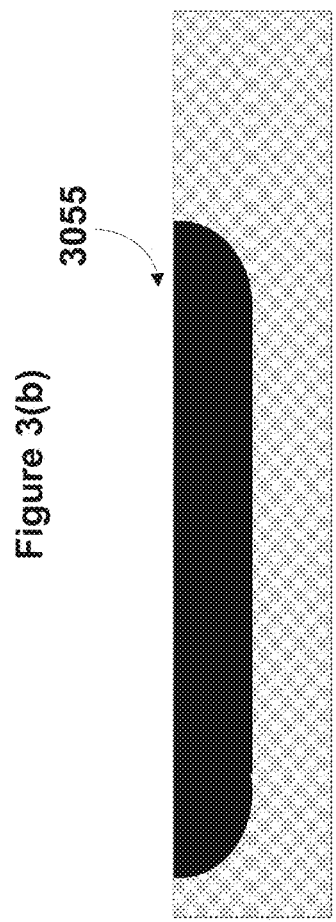

The medical instrument 1044 can be enhanced in another way. As illustrated in FIG. 1(o), a trench 1071 is formed, then the medical instrument (here 1091) is lifted off (see FIG. 1(u)). FIG. 1(u) is a side cross-sectional view and FIG. 1(v) is a front end cross-sectional view of the medical instrument. FIG. 1(w) is a perspective view of a medical instrument (blade device) with a hollow trench 1092, while FIG. 1(k) is a perspective view of a medical instrument (blade device) without a trench 1093. The medical instrument with a trench 1092 and that without a trench 1093 can be coupled together to achieve a new medical instrument 1094 (see FIG. 1(y)). The new instrument 1094 can be a blade with a channel, a syringe or pump with a channel. It can be used to inject materials (e.g., anesthetics or anti-inflammatory drugs) into a tissue, or collect fluid from the tissues, while piercing through or cutting the tissues.

FIG. 2 illustrates another example of the method of this invention for fabricating advanced medical instrument utilizing semiconductor processing technologies. In this example, a substrate 2011 is first patterned using lithography and etch processes (see FIG. 2(a) to FIG. 2(c)). A second material 2033 is next deposited into the recessed area in the substrate 2011 (see FIG. 2(d)), followed by chemical mechanical polishing of the second material 2033 to leave it only in the recessed area of the substrate (see FIG. 2(e)). A third material 2044 is then deposited (see FIG. 2(f)) and patterned using lithography and etch processes (see FIG. 2(g)). Next, another layer of material is deposited. This layer of material can be identical to the second material 2033 or a new material. In FIG. 2(h), the deposited material 2033 on to layer 2044 is identical to the second material 2033. (Optionally, in other examples, this deposited material 2033 can be a different material). Subsequently, the additional deposited layer 2033 can be chemical mechanical polished, leaving only in the recessed area in layer 2044, forming the desired medical instrument 2055 (see FIG. 2(i)). Finally, the medical instrument 2055 is lifted off (see FIG. 2(j)) from the substrate 2011 and the material 2044, e.g., by wet etching or vapor etching.

The fabrication methods of this invention can be used for manufacturing medical instruments with a wide range of desired profiles. Utilizing processes shown in FIG. 1(a)~(g), various profiles of a medical instrument can be obtained (see, e.g., FIG. 3(a)~(c)). The different profiles can be obtained, e.g., using lithography and etch processes. Wet etching chemistry and etching time can vary and be optimized to achieve the desired profile. For example, a shorter wet etching time or an etching chemistry with a lower etch rate (of substrate) can result in a profile shown in FIG. 3(a), while a longer etching time or a chemistry with a faster etch rate (of substrate) results in a rounded, deeper profile shown in FIG. 3(c).

Figure 4:
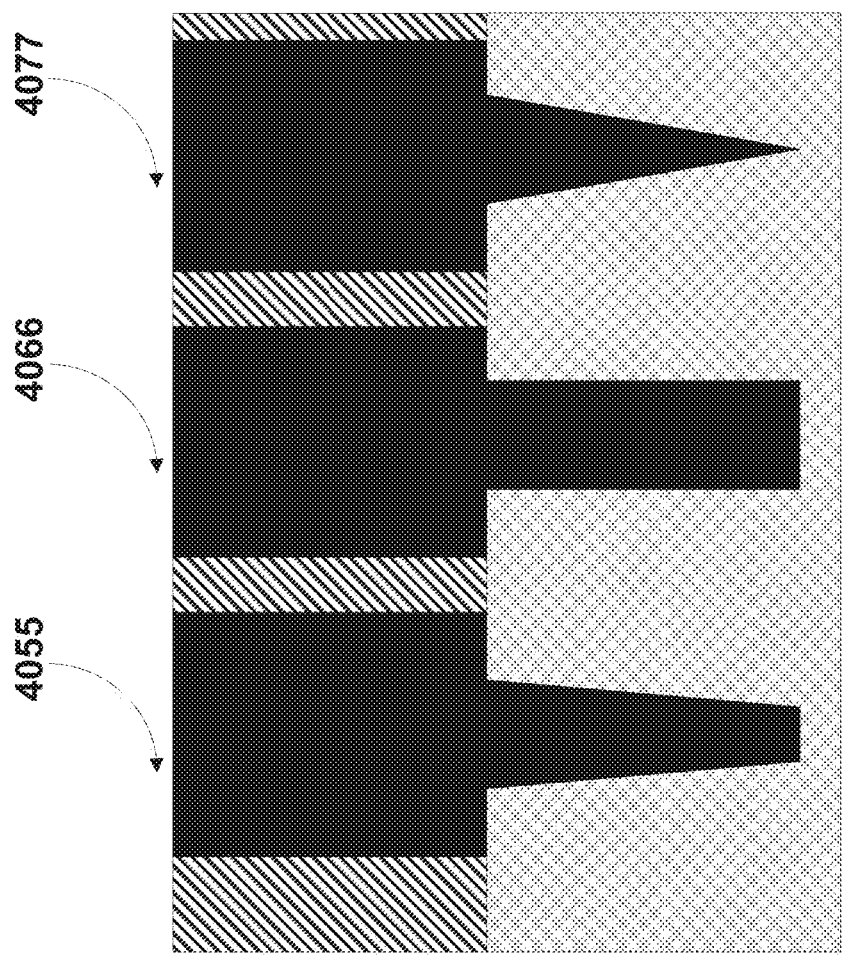
FIG. 4 illustrates some examples of the medical instruments of this invention.

As another embodiment of the methods of this invention, FIG. 4 shows three medical instruments of different profiles (4055, 4066, and 4077) that can be fabricated using similar processes and flow disclosed in FIG. 2.

Figure 5A:
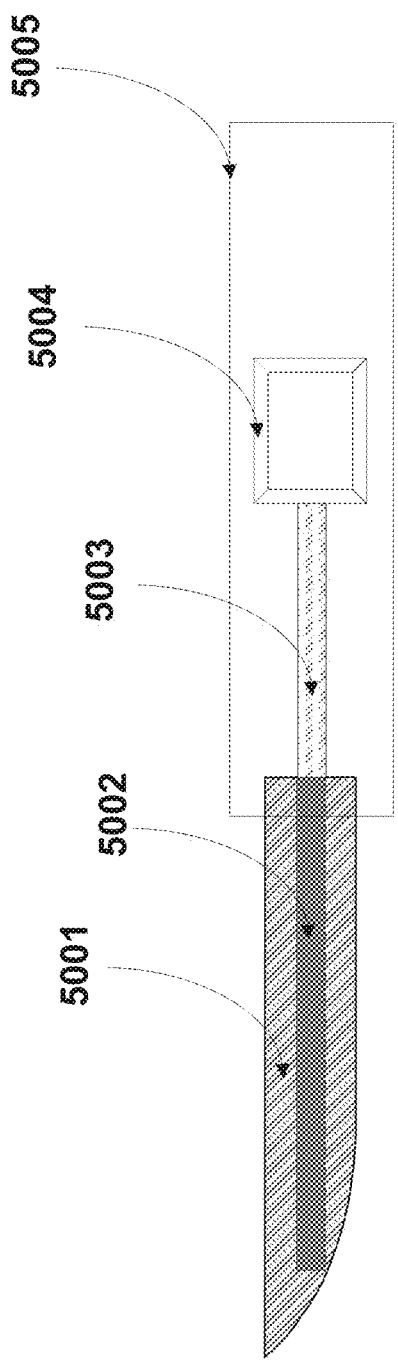
FIG. 5 illustrates an example of a medical device to which a medical instrument of this invention is integrated.

FIG. 5 shows medical devices to which the medical instruments of this invention, or those fabricated by the methods of this invention, are integrated. As illustrated in FIG. 5(a), the micro-surgery system comprises a micro-blade 5001, a probing channel 5002, a data wiring 5003, and a central controlling circuitry unit 5004. The system is packaged in 5005 to support the structural construction.

A sensor can be installed into the probing channel 5002 to detect an electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical or mechanical property, or a combination thereof, of a biological subject. The controlling circuitry comprises microelectronic modules including but not limited to a signal amplifier, a processing unit, and a memory. Information collected by the central controlling circuitry unit 5004 can be transmitted out to servers. A gyro meter or gyro compass can be optional installed in the central controlling circuitry unit 5004, so that the location of the blade can be precisely traced.

Figure 5B:
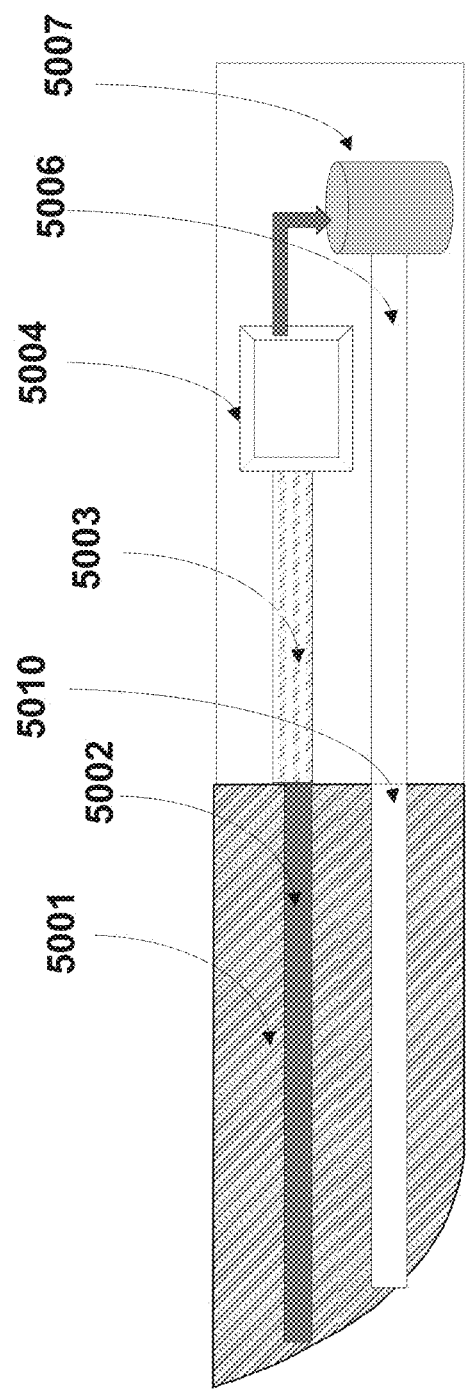

Multiple channels can be integrated in a blade, and multiple blade can be packaged together such that a blade can detect multiple properties of the tissues being operated. As illustrated in FIG. 5(b), a channel 5010 is preserved in the blade and it is connected with a micro-drug-container 5007 by a tunnel 5006. When the biological information of 5002 is analyzed by the central controlling circuitry unit 5004, and in case the drug is needed, the central controlling circuitry unit 5004 will give instructions to 5007 to release a specific volume of drug.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, variations and combinations of the disclosed processes and process flows, and modifications are within the scope of the following claims. All publications referenced herein are incorporated by reference in their entireties.

What is claimed is:

1. A medical instrument fabricated by a method comprising thin film deposition, lithography, etching, polishing, cleaning, diffusion, ion implantation, direct writing, molecular self-assembly, laser ablation, packaging, assembly, or a combination thereof, wherein the size of the medical instrument ranges from 1 angstrom to 10 centimeters, and the method comprises chemical polishing, mechanical polishing, or chemical-mechanical polishing; wherein the medical instrument comprises:
   a blade;
   the blade comprises a thin elongated body, a top flat surface having an end point; a smoothly curved surface, extending from bottom of the thin elongated body toward the top flat surface and contacting the end point of the top flat surface, thereby forming an asymmetry, single-bevel cutting edge; and two opposite side surfaces, each extending between the top flat surface and the curved surface;
   wherein the blade comprises probing channels embedded in and running through the thin elongated body, and the probing channels are substantially parallel with the top flat surface and open through the curved surface.

2. The medical instrument of claim 1, wherein the size of the medical instrument ranges from 5 angstroms to 2 centimeters.

3. The medical instrument of claim 1, wherein the medical instrument is a surgical knife, surgical drill, surgical saw, blade, tongue depressor, medical thermometer, blood sugar meter, artificial heart, fibrin scaffold, stent, treadmill, ultrasound sensor, phototherapy unit, endoscope, human-implantable RFID chip, laparoscopic insufflator, phonocardiograph, radiant warmer, electronic thermometer, breast pump, surgical microscope, ultrasonic nebulizer, temperature monitor, ventilator, auto transfusion unit, cardiac defibrillator, external or internal electrosurgical unit, electro-surgical unit, electro-mechanical surgical unit, external pacemaker, fetal monitor, ventilator, suture, electro-mechanical component, sensor, logic unit for medical applications, memory unit for medical applications, or integrated medical instrument thereof.

4. The medical instrument of claim 1, wherein the probing channel comprises a sensor that is capable of detecting or measuring an electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical, or mechanical property, or a combination thereof, of a biological subject.

5. The medical instrument of claim 1, further comprising one surgical component, a treatment component, a detection unit, a data wiring, or a central controlling circuitry unit.

6. The medical instrument of claim 5, wherein the blade comprises the central controlling circuitry unit, and the central controlling circuitry unit comprises a microelectronic module.

7. The medical instrument of claim 6, wherein the microelectronic module comprises a signal amplifier, a signal lock-in unit, a signal processing unit, a communication unit, a logic processing unit, or a memory device.

8. The medical instrument of claim 7, wherein the communication unit comprises a signal receiver, a signal transmitter, a signal encoding unit, or a signal decoding unit.

9. The medical instrument of claim 5, wherein the blade comprises the central controlling circuitry unit, and the central controlling circuitry unit comprises a gyro meter or a gyro compass.

10. The medical instrument of claim 5, further comprising one or more channels and a package for integrating the device components together.

11. The medical instrument of claim 5, further comprising a micro-drug-container, a channel in the blade, and a tunnel connecting the micro-drug-container and the central controlling circuitry unit.

12. The medical instrument of claim 5, wherein the medical instrument comprises the blade (5001), the probing channel (5002) in the blade, and the data wiring (5003) connecting the probing channel (5002) and the central controlling circuitry (5004).

13. The medical instrument of claim 12, wherein the medical instrument further comprises the micro-drug-container (5007), the channel (5010) in the blade, and the tunnel (5006) connecting the micro-drug-container (5007) with the channel (5010).

14. The medical instrument of claim 1, wherein the instrument is used for a surgery on external wound or an internal disease.

15. The medical instrument of claim 1, wherein the instrument is used for a surgery on eye, skin, brain, cancer, heart, liver, stomach, intestine, or lung.

16. The medical instrument of claim 1, wherein the blade comprises a material selected from the group consisting of polysilicon, piezo-electric materials, optical materials, thermal materials, electro-optical materials, silicon dioxide, doped silicon dioxide, silicon nitride, silicon carbide, glass, diamond, tungsten, titanium, aluminum, molybdenum, tantalum, and metal alloy.

17. The medical instrument of claim 16, wherein the blade comprises a material selected from the group consisting of silicon nitride, silicon carbide, glass, diamond, piezo-electric materials, optical materials, thermal materials, and electro-optical materials.

18. The medical instrument of claim 16, wherein the blade comprises a material selected from the group consisting of tungsten, titanium, aluminum, molybdenum, and tantalum.

19. The medical instrument of claim 1, wherein the blade comprises multiple layers.

20. A medical instrument fabricated by nano technologies, wherein the size of the medical instrument ranges from 1 angstrom to 10 centimeters, and the medical instrument is fabricated by a method comprising chemical polishing, mechanical polishing, or chemical-mechanical polishing; wherein the medical instrument comprises:
   a blade;
   the blade comprises a thin elongated body, a top flat surface having an end point; a smoothly curved surface, extending from bottom of the thin elongated body toward the top flat surface and contacting the end point of the top flat surface, thereby forming an asymmetry, single-bevel cutting edge; two opposite side surfaces, each extending between the top flat surface and the curved surface;
   wherein the blade comprises probing channels embedded in and running through the thin elongated body, and the probing channel are substantially parallel with the top flat surface and open through the curved surface.

* * * * *